US00PP18454P3

(12) United States Plant Patent
Layt

(10) Patent No.: US PP18,454 P3
(45) Date of Patent: Jan. 22, 2008

(54) ***DIANELLA REVOLUTA* PLANT NAMED 'DRG04'**

(50) Latin Name: *Dianella revoluta*
Varietal Denomination: DRG04

(75) Inventor: Todd Anthony Layt, New South Wales (AU)

(73) Assignee: Versascapes, L.L.C., Mt. Pleasant, SC (US)

( * ) Notice: Subject to any disclaimer, the term of this patent is extended or adjusted under 35 U.S.C. 154(b) by 0 days.

(21) Appl. No.: 11/239,545

(22) Filed: Sep. 29, 2005

(65) Prior Publication Data

US 2006/0075532 P1 Apr. 6, 2006

Related U.S. Application Data

(60) Provisional application No. 60/614,795, filed on Sep. 30, 2004.

(51) Int. Cl.
*A01H 5/00* (2006.01)

(52) U.S. Cl. ..... Plt./263
(58) Field of Classification Search ..... Plt./263
See application file for complete search history.

(56) References Cited

U.S. PATENT DOCUMENTS

2006/0075532 P1 * 4/2006 Layt ..... Plt./263

OTHER PUBLICATIONS (Royal Horticultural Society Dictionary of Gardening, 1992, vol. II D–K, McMillan Press, London; Stockton Press, New York, p. 49–50).*

Royal Horticultural Society Dictionary of Gardening, 1992, volt II D–K, McMillan Press, London; Stockton Press, New York, p. 49–50.*

Layt; "*Dianella revoluta* spreading flax lily 'DRG04,'" *Plant Varieties Journal* 16 (4): 123 (Feb. 6, 2004).

Layt; "*Dianella revoluta* spreading flax lily 'DRG04,'" *Plant Varieties Journal* 17 (1): 597–599 (Apr. 28, 2004).

Australian Government, IP Australia, Plant Breeder's Rights; Database entry for Australian Plant Breeders Right Application No. 2003/289; Variety 'DRG04' http://pbr.i-paustralia.optus.com.au/docs/2003289.doc, Oct. 2003.

* cited by examiner

*Primary Examiner*—Anne Marie Grunberg
*Assistant Examiner*—Georgia Helmer
(74) *Attorney, Agent, or Firm*—Myers, Bigel Sibley & Sajovec, P.A.

(57) ABSTRACT

'DRG04' is a distinctive variety of *Dianella revoluta,* which is characterized by the combination of a dense compact clumping habit with red basal shoots and a slight weeping of clumps with age. 'DRG04' is further characterized by its glaucous leaves, which result in a two-toned leaf color when viewed from a distance, with a glossy green upper side leaf color and a dull green (slightly blue-toned) lower side leaf color. When observed up-close the leaves are a yellow-green. 'DRG04' is also distinguished by the ability to be easily and productively propagated by division.

2 Drawing Sheets

Latin name of the genus and species: The Latin name of the novel variety disclosed herein is *Dianella revoluta.*

Variety denomination: The inventive variety of *Dianella revoluta* disclosed herein has been given the varietal denomination 'DRG04'.

BACKGROUND OF THE INVENTION

The present invention relates to a new and distinct perennial Spreading Flax Lilly variety of *Dianella revoluta,* which has been given the varietal denomination of 'DRG04'. Its market class is that of an ornamental grass-like plant. 'DRG04' is intended for use in landscaping and as a decorative grass-like plant.

An application for plant breeders' rights for variety 'DRG04' has been filed with the Australian Plant Breeders' Rights Office, and was first gazetted in the Plant Varieties Journal in October 2003 under Application No. 2003/289.

Parentage. The *Dianella revoluta* variety 'DRG04' was first discovered in October 1996 in an Australian nursery in the state of New South Wales after an extensive breeding program. The parent of 'DRG04', 'Queanbeyan Ecotype' ('DR4000', unpatented), is characterized by tall plant height, broad basal shoot width, weaker plant density, medium leaf size, dull green leaf colour and frequent leaf spotting.

In 1995, *Dianella* species were grown together in an open bed covering approximately 250 square meters of area. They were grown in groups of species and ecotypes including *Dianella revoluta* collected from the Queanbeyan area, and other regions. The other *Dianella* species present were *longifolia, tasmanica* and *caerulea.* The plants were open pollinated with possible assisted pollination from general shaking of flower stems onto each other.

Seeds were collected and sown from the 'Queanbeyan Ecotype' plants in December 1995. Approximately 10,000 plants were grown. In October 1996, using the selection criteria of contrasting upper and lower side leaf colour and dense growth habit, a single plant was identified as having a glossy green upper side leaf colour and dull green lower side leaf colour. This plant was selected, potted into a 140 mm pot for further evaluation, and named 'DRG04'.

Asexual reproduction. 'DRG04' was first asexually propagated by division in April 1997 in the state of New South Wales, Australia. 'DRG04' was asexually reproduced again during November 1997 and April 1998 and confirmed to be stable in character. The distinctive characteristics of the inventive variety, 'DRG04', have remained stable and true to type from generation to generation through successive cycles of asexual reproduction including vegetative division and micropropagation.

SUMMARY OF THE INVENTION

'DRG04' is a distinctive variety of *Dianella revoluta,* which is characterized by the combination of a dense compact clumping habit with red basal shoots and a slight weeping of clumps with age. 'DRG04' is further characterized by its glaucous leaves, which result in a two-toned leaf colour when viewed from a distance, with a glossy green upper side leaf colour and a dull green (slightly blue-toned) lower side leaf colour. When observed up-close the leaves are a yellow-green. 'DRG04' is also distinguished by the ability to be easily and productively propagated by division.

BRIEF DESCRIPTION OF THE FIGURES

The photographs in the drawings were made using conventional techniques and show the colours as true as reasonably possible by conventional photography. Colours in the photographs may differ slightly from the colour values cited in the detailed botanical description, which accurately describe the colours of the new *Dianella revoluta.*

BOTANICAL DESCRIPTION OF THE PLANT

The following is a detailed botanical description of a new and distinct variety of a *Dianella revoluta* ornamental grass-like plant known as 'DRG04'. The descriptions disclosed herein are based upon observations of the plant grown in 140 mm nursery pots and field plots in New South Wales, Australia. The plants were approximately 12-months-old at the time of observation. Except as indicated, all colors cited herein refer to The Royal Horticultural Society Colour Chart (The Royal Horticultural Society, London, 2001 edition).

Those skilled in the art will appreciate that certain characteristics will vary with older or, conversely, younger plants. 'DRG04' has not been observed under all possible environmental conditions. Where dimensions, sizes, colors and other characteristics are given, it is to be understood that such characteristics are approximations or averages set forth as accurately as practicable. The phenotype of the variety may differ with variations in the environment such as season, temperature, light intensity, day length, cultural conditions and the like.

Figure 1:
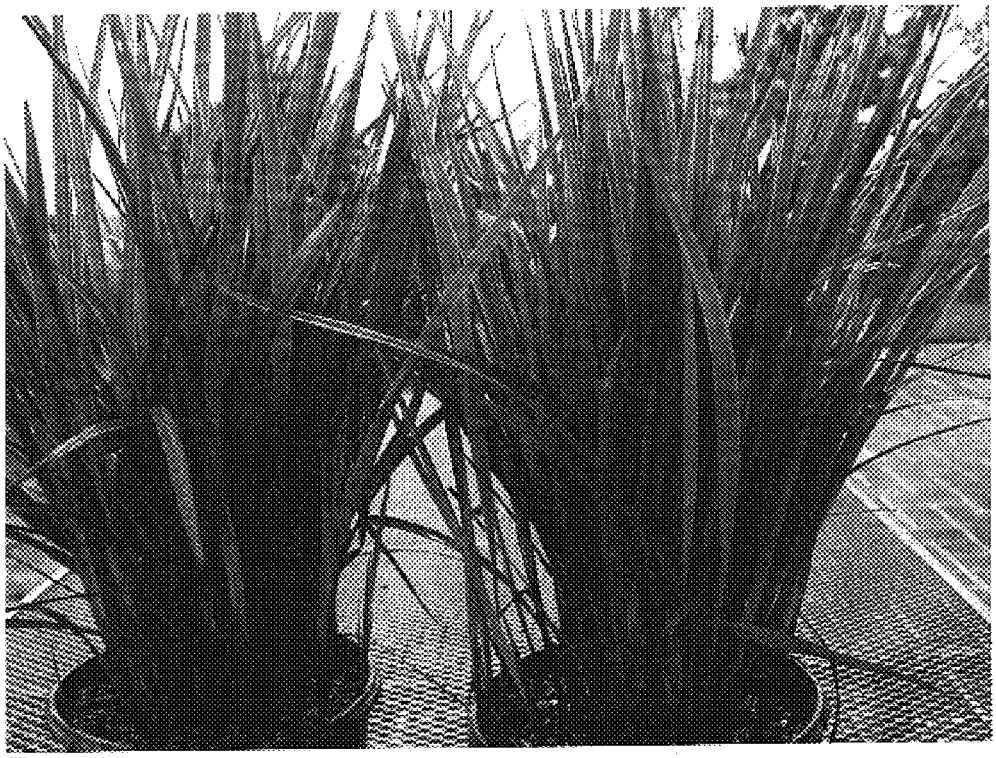
FIG. 1 shows two 'DRG04' plants and illustrates the red basal shoots, two-toned leaf colour, and dense compact growth habit that are characteristic of the variety.
Figure 2:
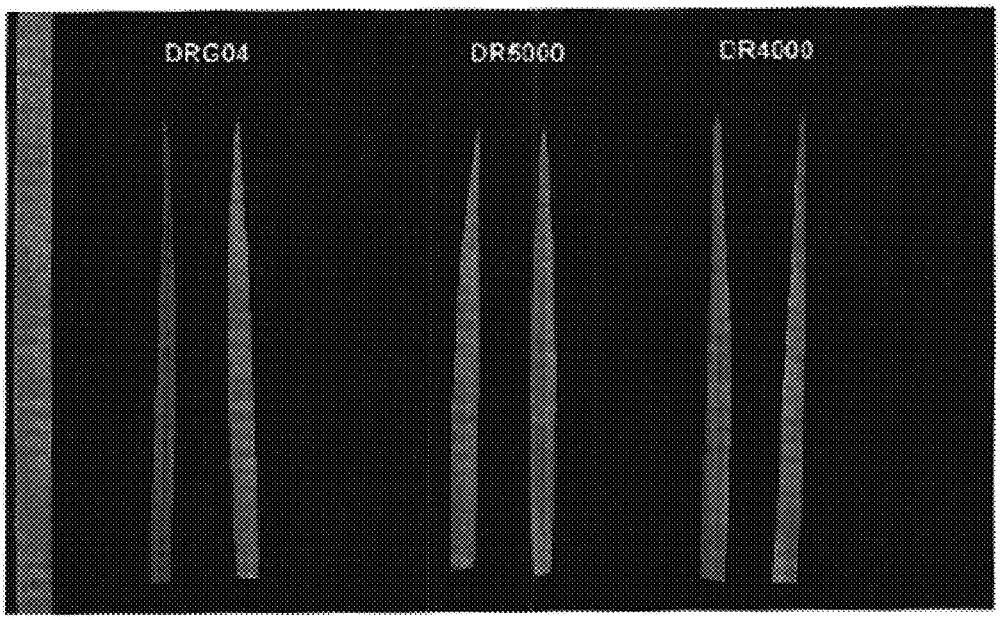
FIG. 2 shows leaf width and glaucosity of 'DRG04' compared with other *Dianella revoluta* varieties, 'DR5000' (U.S. Plant patent application Ser. No. 10/883,942, filed Jul. 2, 2004) and 'DR4000' ('Queanbeyan ecotype', unpatented).

'DRG04' is a perennial *Dianella revoluta* plant, which was produced through an innovative breeding program. After its selection, 'DRG04' was asexually propagated by division and micropropagation. 'DRG04' has a dense compact clumping form with red basal shoots, and a slight weeping of clumps with age. The leaves of 'DRG04' are glaucous and as a result have a two-toned leaf colour when viewed from a distance, with a glossy green upper side leaf colour and dull (slightly blue-toned) green lower side leaf colour. When observed up-close the leaves appear yellow-green. A botanical description of 'DRG04' and a comparison with other varieties of *Dianella revoluta* are provided below. Representative *Dianella revoluta* 'DRG04' plants are shown in FIG. 1.

Technical Description of the Variety

Growth habit: 'DRG04' forms a dense compact clumping tussock. Its growth habit is erect, its height is medium-tall (mean 53.3 cm), and the density of its shoots is strong.

Foliage: Leaf attitude erect, with medium (mean 9.0 mm), upper side colour (waxiness removed) is yellow-green (RHS 146A), the lowers side colour (waxiness removed) is yellow-green (RHS 147B), upper side glaucosity medium, shape ligulate, apex acute, cross section concave, cross-sectional shape with midrib keeled, margin flat to weakly revolute.

Basal shoots: Red (approximately RHS 182A).

Basal sheath: Anthocyanin colour red-brown to purple (RHS 182A proximally and approximately RHS 183A distally with greatest intensity towards the sheath margin). Intensity of colour strong.

Inflorescence: The inflorescence (flower spike) is a panicle with a length (range 60–80 cm). The inflorescence is positioned above the level of the foliage. The flower spike is soft to the touch. Peduncle color is yellow green (approximately RHS 146B–C). Flowering season late spring-summer.

Flowers: The flower buds are 8–10 mm long and 3–4 mm wide. Bud color changes from yellow green (RHS 147B) to violet blue (approximately RHS 89A) prior to opening. Mature flowers have 6 petals with ovate shape. Petal color is violet-blue (approximately RHS 94B). Anther filament color is yellow orange (approximately RHS 23A). Flower diameter range is 10–13 mm. Petal attitude is reflexed.

Fruit: A succulent berry, shape is globose, color of unripe berry is yellow green (RHS 146A) and color of ripe berry is approximately violet blue (RHS 89A), surface texture is smooth and glossy. Seed color is black.

Environmental tolerances: 'DRG04' has shown potential for shade tolerance. The winter hardiness of 'DRG04' is at least to −12 degrees Celsius. 'DRG04' has good winter color retention.

Disease resistance and susceptibility: 'DRG04' has excellent tolerance to pests and diseases. Tolerance to diseases can refer to root rot which is caused by the disease causing organism *Phytophthora.* Tolerance to pests can refer to no damage from snails, slugs, mites, aphids, whitefly, beetles, caterpillars and moths.

These features and other characteristics of the plant are apparent from the figures.

'DRG04' Compared to Other Varieties of *Dianella revoluta*

Grouping characteristics used to identify the most similar varieties of common knowledge to 'DRG04' were medium-tall plant height and dense growth habit. Based on this the 'Queanbeyan Ecotype' ('DR4000') was selected as the most similar suitable comparator. 'DR5000', a sibling cultivar, was also included in the trial. No other similar varieties were identified.

The comparative trial of *Dianella revoluta* 'DRG04' with other *D. revoluta* was conducted in open beds in Summer 2002 through Autumn 2003 in Clarendon, New South Wales, Australia. The plants for this trial were propagated from divisions and planted into 130 mm pots filled with soilless potting mix. Nutrition was maintained with slow release fertilizers and pest and disease treatments were applied as required. The plants did not flower during the trial. Trial design included fifteen pots of each variety arranged in a completely randomized design. Measurements were taken from ten plants at random with one sample taken per plant.

In comparing 'DRG04' with the 'Queanbeyan Ecotype' and 'DR5000', 'DRG04' has an upper side leaf colour of glossy green (making the leaf two-toned as lower side is dull), whereas the 'Queanbeyan Ecotype' (seed parent of 'DRG04') has a dull green upper leaf colour and 'DR5000' has a blue-green upper leaf colour. 'DRG04' has a dense growth habit with many shoots and a somewhat weeping habit at maturity, whereas 'DR5000' has a dense upright growth habit and does not weep at maturity, and the 'Queanbeyan Ecotype' is less dense and more upright. 'DRG04' has a medium width basal shoot, whereas 'DR5000' has a narrow-medium basal shoot width, and the 'Queanbeyan Ecotype' has a broad basal shoot width. 'DRG04' has an improved resistance to spotting compared to other varieties. 'DRG04' divides for nursery production better than any other known *Dianella revoluta,* producing both more divisions and at a higher success rate. 'DRG04' is more compact in height compared to most other *Dianella revoluta,* with the exception of 'DR5000'. Further comparisons are presented in Table I.

TABLE I

Comparison of *Dianella revoluta* varieties

| | 'DRG04' | 'DR5000' | 'Queanbeyan Ecotype' ('DR4000') |
|---|---|---|---|
| PLANT: HEIGHT (cm) - | | | |
| Mean | 53.3 | 24.7 | 57.1 |
| Std deviation | 2.4 | 1.9 | 4.9 |
| LSD/sig | 3.82 | P ≦ 0.01 | ns |
| PLANT: DENSITY OF SHOOTS | | | |
| | strong | strong | weak |
| LEAF: WIDTH (mm) | | | |
| Mean | 9.0 | 9.1 | 10.4 |
| Std deviation | 1.0 | 1.0 | 1.0 |
| LSD/sig | 1.13 | ns | P ≦ 0.01 |
| LEAF: GLAUCOSITY | | | |
| | medium | strong | medium |
| LEAF: COLOUR (RHS 2001, where denoted * better match with 1995 chart) | | | |
| Upper side | 146A | 147A | 146A |
| Lower side | 1478 | 189A* (1995) | 146C-D |
| LEAF: CROSS SECTION | | | |
| | concave | concave | flat-revolute |
| BASAL SHEATH INTENSITY OF COLOUR | | | |
| | strong | medium | medium |

That which is claimed is:

1. A new and distinct variety of *Dianella revoluta* plant named 'DRG04', substantially as described and illustrated herein.

* * * * *